United States Patent [19]

Marras et al.

[11] Patent Number: 5,143,088
[45] Date of Patent: Sep. 1, 1992

[54] APPARATUS FOR MONITORING THE MOTION COMPONENTS OF THE SPINE

[75] Inventors: William S. Marras, 225 Beach Trail Ct., Powell, Ohio 43065; Shelby W. Davis, Amlin, Ohio; Robert J. Miller, Westerville, Ohio; Gary A. Mirka, Brecksville,, Ohio

[73] Assignee: William S. Marras, Powell, Ohio

[21] Appl. No.: 696,370

[22] Filed: May 6, 1991

Related U.S. Application Data

[63] Continuation of Ser. No. 551,649, Jul. 11, 1990, Pat. No. 5,012,819, which is a continuation of Ser. No. 336,896, Apr. 12, 1989, abandoned.

[51] Int. Cl.$^5$ ............................................. A61B 5/11
[52] U.S. Cl. ..................................... 128/781; 33/512
[58] Field of Search ..................... 128/774, 781, 782; 33/511, 512

[56] References Cited

U.S. PATENT DOCUMENTS

| | | |
|---|---|---|
| 3,608,541 | 9/1971 | Hall . |
| 3,908,279 | 9/1975 | Yoslow et al. . |
| 3,991,745 | 11/1976 | Yoslow et al. . |
| 4,108,164 | 8/1978 | Hall, Sr. . |
| 4,461,085 | 7/1984 | Dewar et al. . |
| 4,528,990 | 7/1985 | Knowles . |
| 4,655,227 | 4/1987 | Gracovetsky . |
| 4,699,156 | 10/1987 | Gracovetsky . |
| 4,768,779 | 9/1988 | Oehman, Jr. et al. . |
| 4,800,897 | 1/1989 | Nilsson . |
| 4,971,069 | 11/1990 | Gracovetsky . |

FOREIGN PATENT DOCUMENTS

WO87/00026 1/1987 PCT Int'l Appl. .
WO89/11247 11/1989 PCT Int'l Appl. .
455567 5/1988 Sweden .

OTHER PUBLICATIONS

"Flexibility and Velocity of the Normal and Impaired Lumbar Spine"; Archives of Physical Medicine and Rehabilitation, vol. 67, Apr., 1986, pp. 213-217.
Operating Manual for Ady-Hall Lumbar Monitor entitled "Lumbar Hygiene", comprising cover sheet and 16 pages, dated May 13, 1983.
"The Low Back Machine That Moves Like The Low Back", Isotechnologies Inc., one page.

*Primary Examiner*—Ruth S. Smith
*Attorney, Agent, or Firm*—Bell, Seltzer, Park & Gibson

[57] ABSTRACT

An apparatus is disclosed for monitoring the functional motion characteristics of the spine in each of three planes. The apparatus is designed to be mounted on the back of a patient, and it includes an exoskeleton of T-shaped elements which resemble the spinous process and the transverse process of the spine. The elements each include a central bore for receiving a cable, and three separate openings for receiving a wire therethrough. The cable is attached to a potentiometer which measures twisting movement of the spine, and each of the three wires is attached to a separate potentiometer so as to measure flexing in the and sagittal and lateral planes. The signals from the potentiometers are processed so as to provide, for each of the three planes, a measurement of the angular position of the spine as a function of time, the angular velocity as a function of time, and the angular acceleration as a function of time.

6 Claims, 4 Drawing Sheets

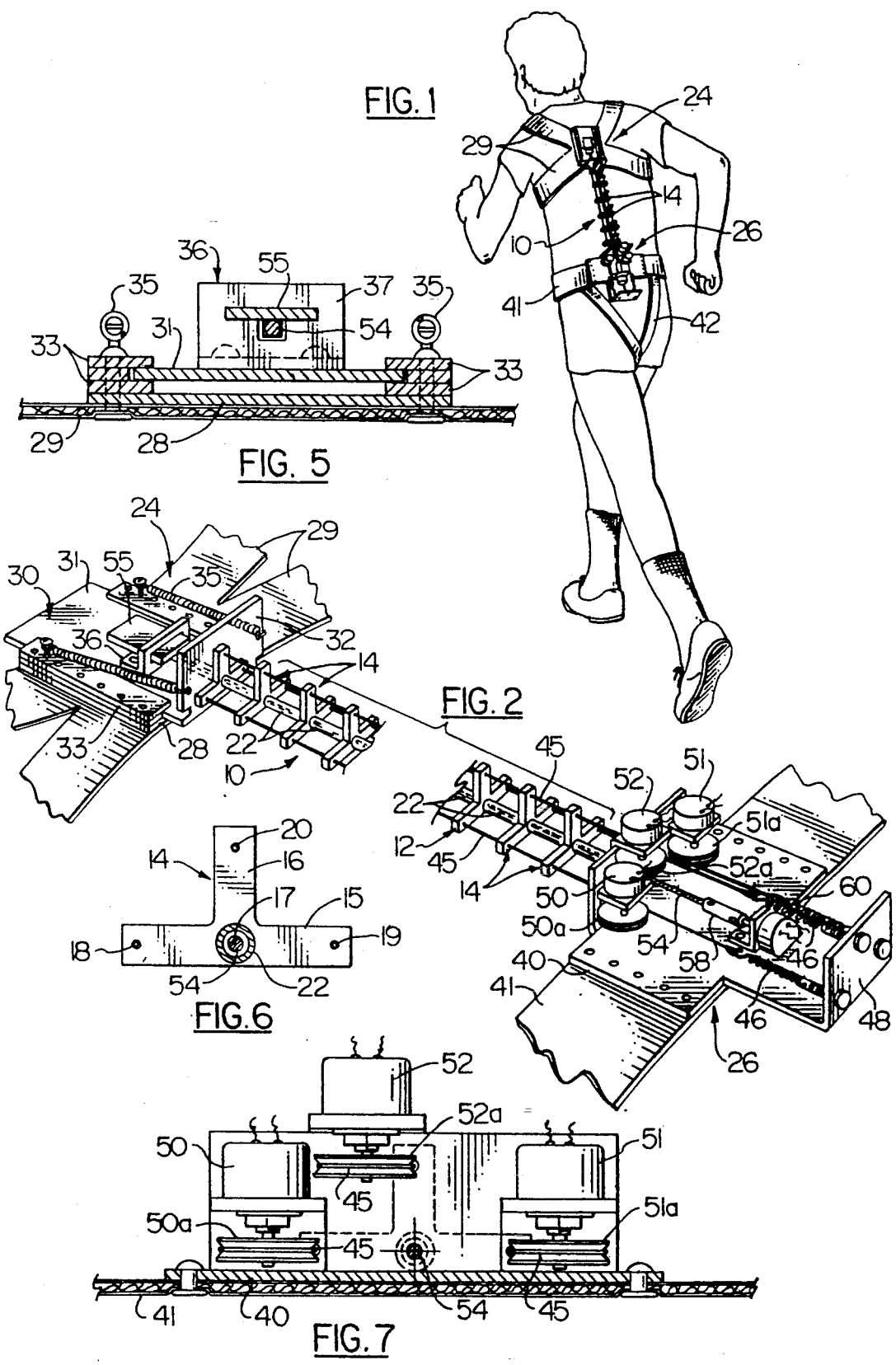

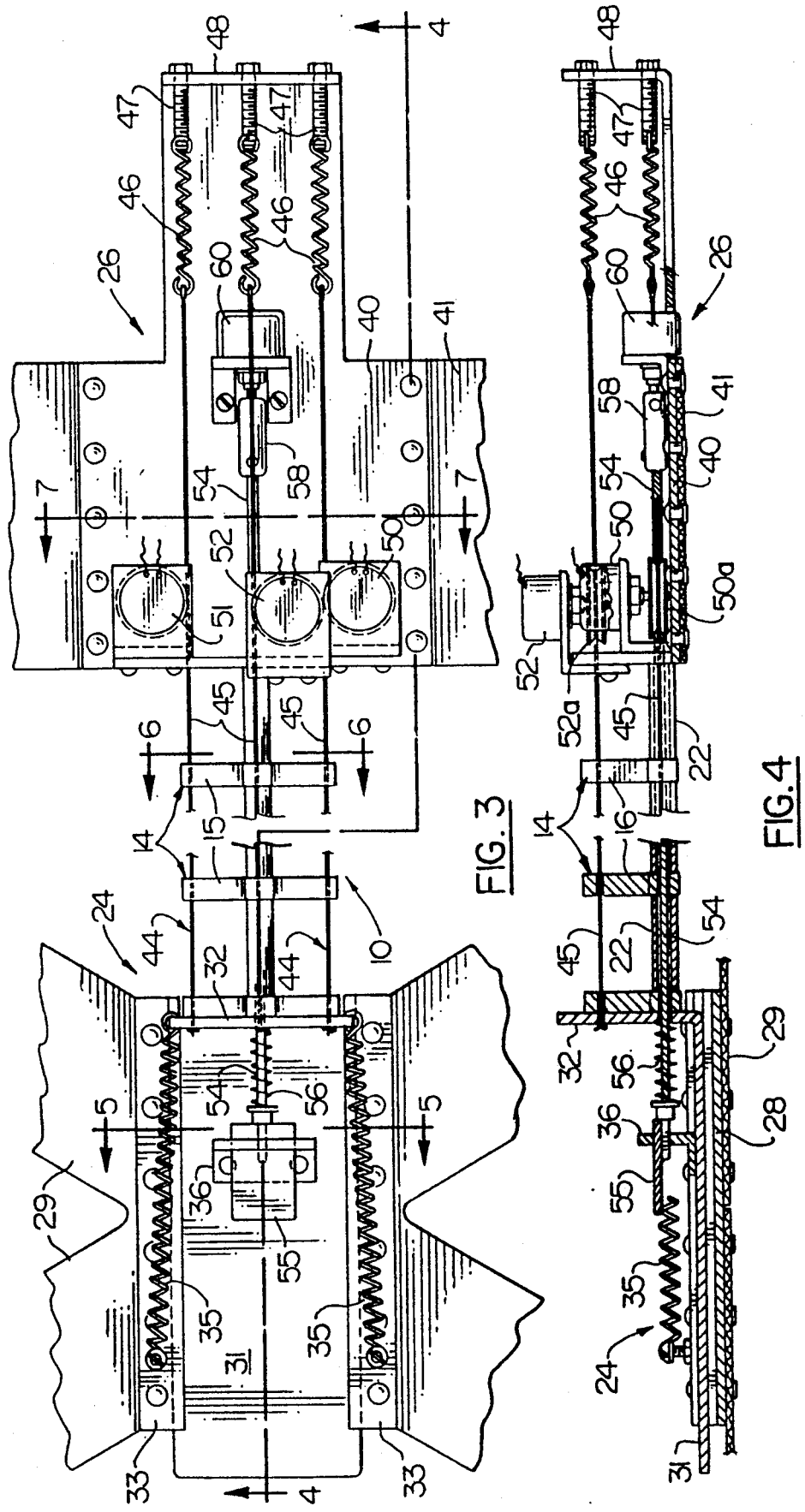

APPARATUS FOR MONITORING THE MOTION COMPONENTS OF THE SPINE

CROSS REFERENCE TO RELATED APPLICATIONS

This application is a continuation of application Ser. No. 07/551,649, filed Jul. 11, 1990, now U.S. Pat. No. 5,012,819, issued May 7, 1991, and which in turn is a continuation of application Ser. No. 07/336,896, filed Apr. 12, 1989, now abandoned.

BACKGROUND OF THE INVENTION

The present invention relates to an apparatus adapted to be mounted on the back of a patient and for monitoring the motion components of the spine during movement of the patient.

In diagnosing physical injuries or deterioration of the human spine, it is common to utilize a small goniometer which is attached on the back of the patient, and which indicates the static posture of the patient. Such instruments are adequate for documenting the bend or curvature of the spine, but they are incapable of documenting the motion or velocity or acceleration components, which are also useful in diagnosis.

More sophisticated diagnostic devices are also known which are capable of measuring the velocity components of the spine during movement of the patient. These velocity measuring devices are designed to permit the patient to physically enter the device, and thus they are very large and quite expensive. Also, in view of their size, these devices have a substantial moment of inertia which tends to mask the motion patterns of the patient.

It is accordingly an object of the present invention to provide a relatively simple and inexpensive apparatus for monitoring the motion components of the human spine, and which is useful in diagnosing a physical injury or deterioration of the spine.

It is also an object of the present invention to provide an apparatus of the described type and which is adapted to be mounted on the back of the patient so as not to interfere with normal body movements, and which can be worn "on the job" so as to permit an analysis of the motion components which are required to be performed by a worker.

These and other objects and advantages of the present invention are achieved in the embodiment illustrated herein by the provision of an apparatus which comprises an elongate exoskeleton comprising a plurality of generally flat elements disposed in a longitudinally spaced apart arrangement. A spacer is disposed between each adjacent pair of elements for maintaining the separation of the elements, and the spacers are longitudinally aligned and define a central longitudinal axis. A plurality of openings extend longitudinally through each of said elements, with each of said openings of each element being spaced from the central axis and being longitudinally aligned with a corresponding opening of the remaining elements.

The apparatus further comprises support means for supporting the exoskeleton on the back of a patient and so that the exoskeleton is generally aligned along the spine. The support means comprises a top plate, strap means for releasably securing the top plate on the upper back of the patient, a base plate, belt means for releasably securing said base plate on the lower back of the patient, and wire means extending longitudinally through each of the aligned openings of the elements, with each of said wire means being resiliently extensible in length, and with the opposite ends of each wire means being respectively attached to the top plate and the base plate. Thus, flexing movement of the exoskeleton caused by the movement of the patient causes each of said wire means to selectively change in length. The apparatus also includes movement signaling means mounted to the support means for detecting longitudinal movement of each of the wire means caused by changes in the length thereof, and for providing an output signal representative of such movement.

In the preferred embodiment as illustrated herein, there are three openings in each of the elements and which are disposed in a triangular arrangement. Also, each of the elements further includes a bore extending therethrough which is aligned with the central axis, and a cable means extends longitudinally through the bores of the elements. One end of the cable means is fixedly mounted to the top plate, and the other end is rotatably mounted to the base plate. Further, a rotation signaling means is mounted to the base plate for detecting rotation of the cable means in either direction and providing an output signal representative thereof.

The present invention thus permits three planes of movement to be simultaneously monitored, namely, the sagittal (i.e. forward and back), the transverse (i.e. twisting), and the lateral planes. In accordance with a further aspect of the invention, the monitored motion characteristics in each such plane include the angular position of the spine as a function of time, the angular velocity as a function of time, and the angular acceleration as a function of time.

BRIEF DESCRIPTION OF THE DRAWINGS

Some of the objects and advantages of the present invention having been stated, others will appear as the description proceeds, when taken in conjunction with the accompanying drawings, in which FIG. 1 is a perspective view illustrating the apparatus of the present invention mounted on the back of a patient during use;

FIG. 2 is a fragmentary perspective view of the apparatus;

FIGS. 3 and 4 are top plan and side elevation views of the apparatus respectively, with FIG. 4 being taken substantially along the ling 4—4 of FIG. 3;

FIGS. 5, 6, and 7 are sectional views taken respectively along the lines 5—5, 6—6, and 7—7 of FIG. 3;

DETAILED DESCRIPTION OF THE PREFERRED EMBODIMENT

Figure 8:
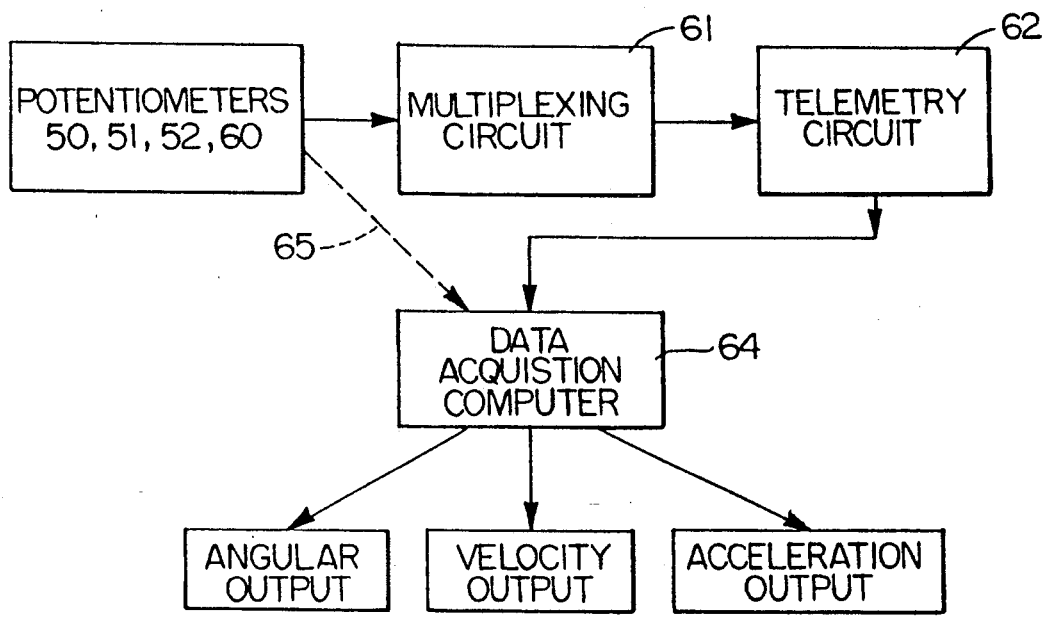
FIG. 8 is a schematic flow diagram illustrating a preferred embodiment of the signal processing system of the present invention.

Referring more particularly to the drawings, FIG. 1 illustrates an apparatus 10 which embodies the present invention and which is shown mounted on the back of a patient. In the illustrated embodiment, the apparatus is used to monitor the movement of the spine, and particularly the lumbar spine.

The apparatus 10 includes an elongate exoskeleton 12 comprising a plurality of generally flat, T-shaped elements 14 which are disposed in a longitudinally spaced apart arrangement. As best seen in FIG. 6, each element 14 is composed of a horizontal base leg 15, and an upright leg 16. Also, each element includes a central bore 17 at the intersection of the two legs, with the bore 17 extending longitudinally therethrough. Further, first and second smaller openings 18, 19 are positioned at the respective ends of the horizontal base leg on opposite sides of the central bore 17, and such that the bore 17 and the first and second openings 18, 19 lie substantially in a common horizontal plane. A third opening 20 is provided adjacent the free end of the upright leg 16, and such that the third opening 20 is equally spaced from the first and second openings, and the first, second, and third openings are disposed in a triangular arrangement.

The elements 14 are each disposed in parallel transverse planes, and they are aligned along the longitudinal direction. The central bores 17 of the elements are also longitudinally aligned to define a central longitudinal axis. Similarly, the first, second, and third openings of each element are longitudinally aligned with the corresponding openings of the other elements.

A tubular spacer 22 is disposed between each adjacent pair of elements 14 for maintaining the separation thereof, and with the spacers 22 being longitudinally aligned with the central bores and thus with the central axis. The spacers 22 are not fixedly attached to the elements, but are supported in the described position by the structure set forth below, and so as to permit relative motion of the elements 14 in all axes.

The apparatus 10 also includes support means for supporting the exoskeleton 12 on the back of a patient and so that the exoskeleton is generally aligned along the spine as best seen in FIG. 1. This support means includes an upper assembly 24, and a lower assembly 26. More particularly, the upper assembly 24 includes a support plate 28, which is fixedly attached to a harness 29 which is in the form of a figure eight and which loops about the shoulders of the patient. The harness 29 is preferably fabricated from a semi-rigid material, such as "Orthoplast" material sold by Johnson & Johnson, and which is open in the front, and with the front being closed by suitable straps having VELCRO interconnection means (not shown). This construction provides a stable mounting of the exoskeleton 12 to the upper body of the wearer.

The upper assembly 24 also includes a top plate 30 which is slideably connected to the support plate 28. In this regard, the top plate 30 has an L-shaped configuration so as to include a flat lower segment 31 and an upright segment 32. The support plate 28 includes opposing side members 33 which define opposing slots, and the lower segment 31 of the top plate fits within the slots as best seen in FIG. 5, and so that the top plate is free to slide in the longitudinal direction with respect to the support plate. A pair of springs 35 extend between the side members 33 and the upright segment 32 of the top plate, and act to bias the top plate upwardly with respect to the support plate and the strap. Also, the lower segment 31 of the top plate mounts a bracket 36 having an upright leg 37 which contains a horizontal slot, for the purposes described below.

The lower assembly 26 includes a base plate 40 which is mounted to a belt 41, and such that the belt releasably secures the base plate on the lower back of the patient. In the illustrated embodiment, the belt 41 comprises a waist band which may also be composed of "Orthoplast" material, and, which may be divided in front and include VELCRO interconnection means (not shown). Also, a pair of straps 42 are attached to the waist band and extend between the legs of the patient.

The apparatus 10 of the present invention also includes wire means 44 extending longitudinally through each of the three aligned openings 18, 19, 20 of the elements 14, and with each of the wire means 44 being resiliently extensible in length. More particularly, each of the wire means includes a non-extensible solid wire 45, and an extensible spring 46 attached to one end of the wire. Each wire 45 has its opposite end fixed to the upright segment 32 of the top plate 30, and each wire 45 runs through all of the elements and to a point adjacent the lower portion of the base plate 40 where it joins one end of the spring 46. The opposite end of the spring 46 is connected to a threaded member 47, which in turn is joined to the upright flange 48 of the base plate 40.

Movement signaling means is mounted on the base plate for detecting longitudinal movement of each of the wire means caused by changes in length thereof, and for providing an output signal representative of such movement. In the illustrated embodiment, this signaling means comprises three electrical potentiometers 50, 51, 52 mounted to the base plate. Each potentiometer includes a pulley 50a, 51a, 52a respectively, and the associated wire 45 is wrapped about the pulley so that any longitudinal movement of the wire with respect to the base plate causes the associated pulley and potentiometer to rotate.

The apparatus 10 further includes a cable 54 extending longitudinally through the aligned bores 17 of the segments and coaxially through the spacers 22. The cable 54, which preferably comprises a piano wire, has one end attached to a plate 55 which is slideably received in the slot of the bracket 36 as best seen in FIG. 5, and a spring 56 is interposed between the end of the cable and the upright segment 32 of the top plate. The slideable interconnection formed between the plate 55 and the bracket 36 accommodates the elongation of the spine which occurs when the patient bends forward, while maintaining cable 54 in a fixed rotational orientation at its upper end. The opposite end of the cable 54 is fixed to a connector 58, and the connector 58 in turn is fixed to the output shaft of a fourth potentiometer 60 mounted on the base plate 40. Thus any twisting of the exoskeleton about the central axis causes the potentiometer 60 to rotate. As will be understood by those skilled in the art, other movement sensors may be employed as an alternative to the illustrated potentiometers, such as optical encoders.

Figure 9:
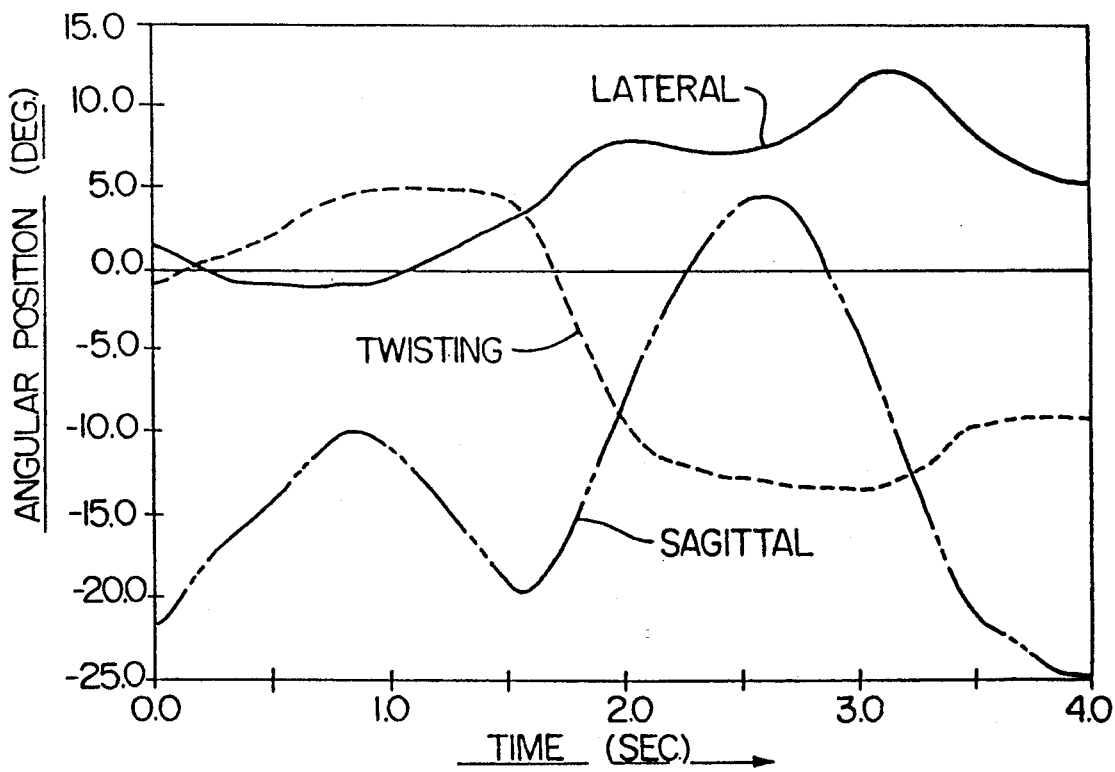
FIGS. 9, 10, and 11 are diagrams illustrating a typical output of the angular position, velocity, and acceleration as a function of time, respectively.
Figure 10:
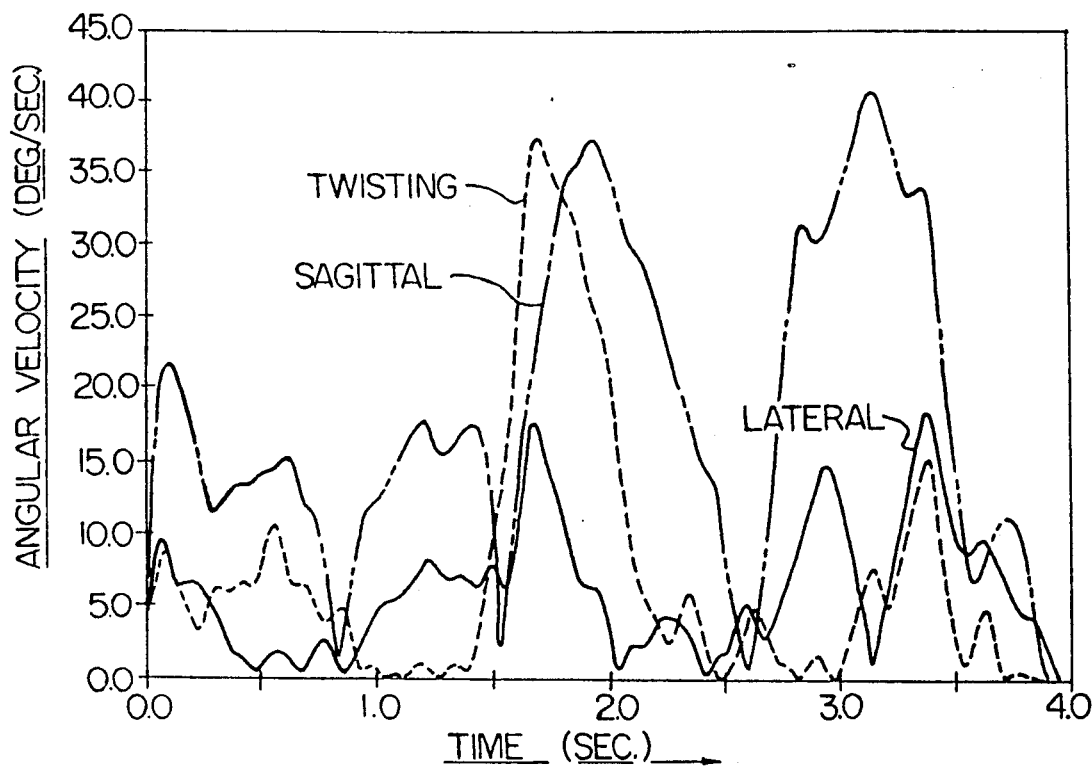
Figure 11:
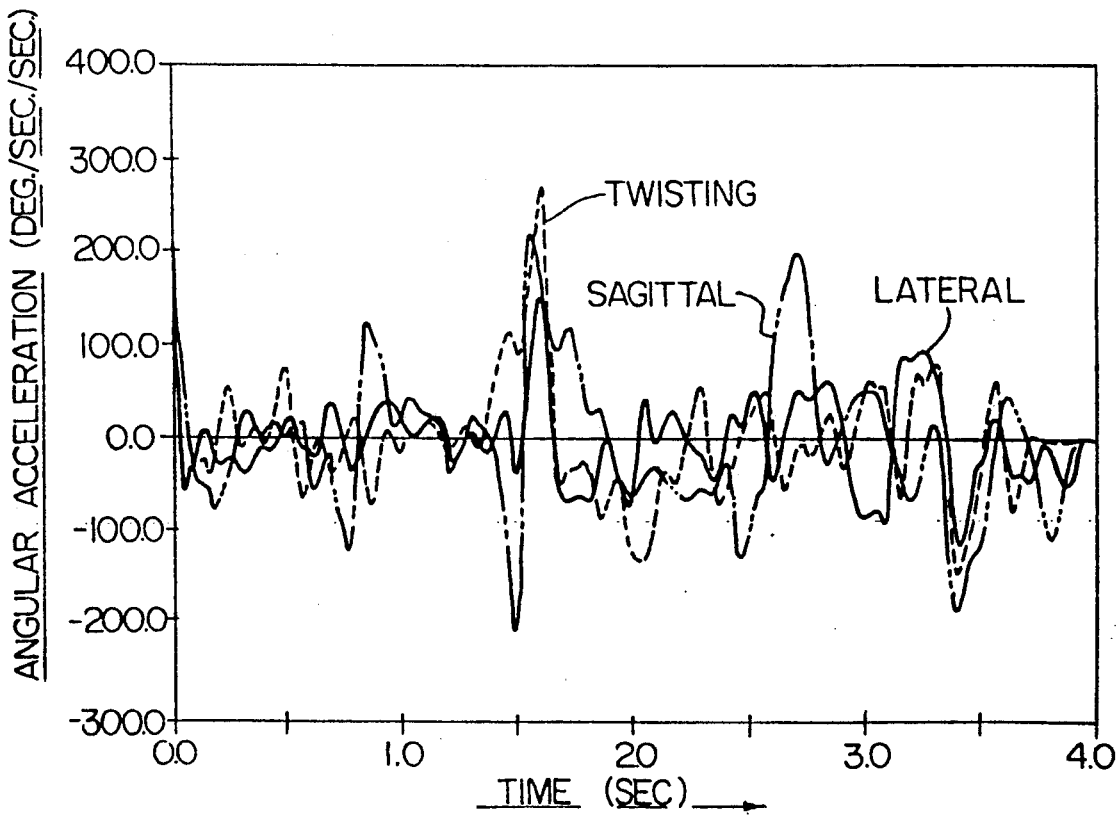

As schematically illustrated in FIG. 8, the apparatus of the present invention may further include a multiplexing circuit 61 and a telemetry circuit 62 mounted on the base plate 40 of the apparatus. The multiplexing circuit 61 provides power to the four potentiometers, and sequentially mixes the signals from each of the potentiometers. The telemetry circuit 62 then transmits the mixed signals to a data acquisition computer 64 which demultiplexes the signal received from the telemetry circuit. Further, the data acquisition computer 64 may be programmed to smooth the data and convert the signals to angular position via a calibration, and then store the resulting data. The software then sorts the data for each of three planes of movement, namely the sagittal, transverse, and lateral planes. The motion characteristics in each plane include the angular position of the spine relative to the position to the pelvis considered as a function of time, and as illustrated in FIG. 9. This information may then be differentiated to determine the angular velocity of the spine as a function of time and as illustrated in FIG. 10, as well as the angular acceleration of the spine as a function of time and as illustrated in FIG. 11.

As an alternative to the above described signal processing system, the potentiometers may be hardwired directly to the computer 64 as schematically illustrated by the dashed line 65 in FIG. 8, thus bypassing the multiplexing circuit 61 and the telemetry circuit 62.

A calibration table is used to calibrate the apparatus of the present invention. Specifically, the apparatus is placed in the calibration table and the position of the apparatus is moved to a large number of different positions in space. The four potentiometer voltages associated with each of these positions is then recorded in the computer, and these voltages are then used to uniquely described the positions of the apparatus in space. A mathematical regression model is then used to estimate a best fit plane between the potentiometer voltages and the position in space of the apparatus. Therefore, when the apparatus is in use the voltage readings from the four potentiometers are compared to the model and the exact position of the apparatus in space is determined. As noted above, this information is then differentiated to determine instantaneous angular velocity and acceleration.

In the drawings and specification, there has been set forth a preferred embodiment of the invention, and although specific terms are employed, they are used in a generic and descriptive sense only and not for purposes of limitation.

That which is claimed is:

1. An apparatus for monitoring the motion components of the spine during movement of a patient, comprising:

movement sensing means for simultaneously monitoring movement in each of three separate planes, support means for mounting said movement sensing means on the back of a patient such that said movement sensing means simultaneously monitors movement of the spine of the patient in each of the lateral, sagittal, and transverse planes, and such that the patient is fully ambulatory, and means connected to said movement sensing means for producing an output signal representative of the angular position of the spine in each of said lateral, sagittal, and transverse planes when said movement sensing means is mounted on the back of the patient.

2. The apparatus as defined in claim 1 wherein said output producing means further comprises means for producing an output signal representative of the angular velocity in each of said lateral, sagittal, and transverse planes.

3. The apparatus as defined in claim 2 wherein said output producing means further comprises means for producing an output signal representative of the angular acceleration in each of the lateral, sagittal, and transverse planes.

4. The apparatus as defined in claim 3 wherein said output producing means further comprises means for displaying the angular position vs time, the angular velocity vs time and the angular acceleration vs time in each of the lateral, sagittal, and transverse planes.

5. The apparatus as defined in claim 2 wherein said output producing means further comprises means for displaying the angular position vs time and the angular velocity vs time in each of said lateral, sagittal, and transverse planes.

6. The apparatus as defined in claim 1 wherein said output producing means further comprises means for displaying the angular position vs time in each of said lateral, sagittal, and transverse planes.

* * * * *